United States Patent [19]

Hagstrom et al.

[11] 3,991,090

[45] Nov. 9, 1976

[54] METHOD OF PREPARING MOLYBDENUM DERIVATIVE COMPOUND CATALYSTS FOR EPOXIDATION REACTIONS

[75] Inventors: Richard A. Hagstrom, Cheshire; John A. Herbst, Madison; Robert J. Fairbrother, Wallingford, all of Conn.

[73] Assignee: Olin Corporation, New Haven, Conn.

[22] Filed: July 11, 1975

[21] Appl. No.: 595,045

[52] U.S. Cl. .......................... 260/429 J; 260/429 R
[51] Int. Cl.² ........................................... C07F 11/00
[58] Field of Search .................... 260/429 R, 429 J; 252/431 R

[56] References Cited
UNITED STATES PATENTS

| | | |
|---|---|---|
| 2,795,552 | 6/1957 | Abbott et al. .................. 260/429 X |
| 3,121,059 | 2/1964 | De Young et al. ............. 260/429 X |
| 3,285,942 | 11/1966 | Price et al. ........................... 260/429 |
| 3,480,563 | 11/1969 | Bonetti et al. .................. 252/431 R |
| 3,668,227 | 6/1972 | Mattucci et al. ................. 260/429 J |
| 3,822,321 | 7/1974 | Maurin et al. .................. 252/431 R |

*Primary Examiner*—Helen M. S. Sneed
*Attorney, Agent, or Firm*—F. A. Iskander; T. P. O'Day

[57] ABSTRACT

A method of preparing molybdenum derivative compound catalysts for epoxidation reactions is described wherein an oxygen-containing molybdenum compound is reacted with an organic compound having vicinal hydroxyl groups in the presence of a hydrohalic acid selected from hydrofluoric acid, hydrochloric acid, hydrobromic acid and hydroiodic acid.

10 Claims, No Drawings

METHOD OF PREPARING MOLYBDENUM DERIVATIVE COMPOUND CATALYSTS FOR EPOXIDATION REACTIONS

This invention relates to molybdenum derivative compounds represented generically by the formulas:

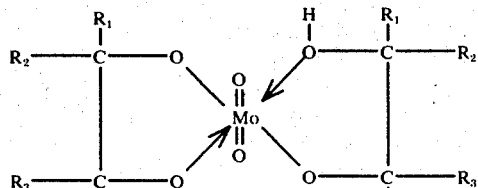

(I)

and

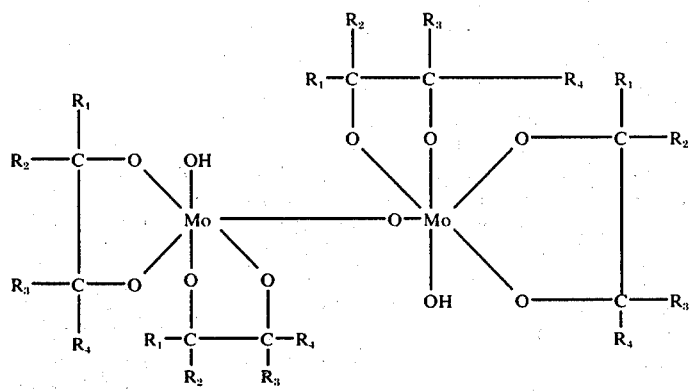

(II)

wherein each of $R_1$, $R_2$, $R_3$ and $R_4$, which may be the same or different, is a hydrogen atom, an unsubstituted or substituted hydrocarbon radical having from one to 10 carbon atoms, or a group having one of the formulas:

—COOR, —CN, —CONH$_2$, and —NO$_2$, where R is a hydrocarbon radical having from one to 10 carbon atoms, or where $R_1$ and $R_4$, and/or $R_2$ and $R_3$ may form a bivalent hydrocarbon radical. More specifically, the present invention relates to a novel method of making the above compounds in significantly higher yields than the yields obtained by the prior art preparation methods.

The molybdenum derivative compounds prepared by the method of the present invention may be used as catalysts in the manufacture of organic epoxides by the reaction of peroxidic compounds with unsaturated organic starting materials. The compounds are particularly useful in the oxidation of olefins with hydrogen peroxide to obtain alkylene epoxides, such as in the processes described in U.S. Pat. No. 3,778,451 to Poite, incorporated herein by reference.

It has been disclosed in U.S. Pat. No. 3,668,227 to Mattucci et al that the compounds of Formula (I) and Formula (II) above are particularly useful as oxidation catalysts due to the improved kinetics and yields obtained as compared to other catalysts. Additionally, these compounds have been found to substantially enhance the stability of the peroxidic compound and retard the loss of active oxygen during the oxidation reaction.

It has now been discovered that the compounds of Formula (I) and Formula (II) above may be made in higher yields and therefore in a more economical manner than that disclosed in the Mattucci et al patent mentioned above. Specifically, the method of the present invention involves a method of making the compounds of Formulas (I) and (II) wherein an oxygen-containing molybdenum compound and an appropriate hydroxylated compound are reacted in the presence of a small but effective amount of a hydrohalic acid.

In the method of the present invention, a molybdenum compound in which oxygen is directly attached to the molybdenum atom is reacted with organic compounds having adjacent hydroxyl groups. The oxygen-containing molybdenum compound may be, for example, an organic molybdenum compound such as molybdenum acetylacetonate, or, for example, the ammonium salt or molybdic acid, or it may be one containing only oxygen and molybdenum atoms, i.e., one of the molybdenum oxides, e.g., molybdenum dioxide, molybdenum sesquioxide, molybdenum trioxide or mixtures of these. The preferred molybdenum starting material is molybdenum trioxide.

The organic compounds having adjacent hydroxyl groups, and which are reacted with the oxygen-containing molybdenum compound, include the vicinal alkylene glycols having from about 2 to about 12, and preferably about 2 to about 6 carbon atoms in the molecule. Preferred among these are propylene glycol and the 1,2 glycols of butylene, pentene and hexene, as well as cyclic compounds, e.g., 1,2 cyclohexanediol.

The reaction catalyst employed in the method of the present invention is a hydrohalic acid selected from hydrofluoric acid, hydrochloric acid, hydrobromic acid and hydroiodic acid. Preferred are hydrofluoric and hydrochloric acids, especially hydrochloric acid. Generally, at least about 0.05 moles, for example, about 0.05 to about 1 or more moles, of the hydrohalic acid per mole of molybdenum atoms present in the reaction mixture is employed as the reaction catalyst. Preferably about 0.2 to about 0.5 moles are used.

The oxygen-containing molybdenum compound, the organic compound having adjacent hydroxyl groups and the hydrohalic acid catalyst are combined and reacted at temperatures from about −20° C. to about 110° C., preferably about 30° C. to about 100° C. Generally, about 2 to about 20 moles, and preferably about 3 to about 5 moles, of organic compound are combined with the oxygen-containing molybdenum compound on a per mole of molybdenum atoms basis. The reaction may be performed in a short period of time, e.g., about 2 hours, or over a longer period of time., e.g., 72 hours, but preferably the reaction is completed to a commercially acceptable degree in about 6 to about 8 hours.

The oxygen-containing compound and the organic compound may be reacted in the absence or presence of a solvent and any solvent may be used provided that it is inert to the reactants and products of the reaction. Among the useful solvents are the hydrocarbon inert solvents, such as benzene and toluene, as well as alcohols, such as butyl or amyl alcohol. In a preferred embodiment, the reactants themselves constitute solvent.

The products obtained by the method of the present invention are compounds represented structurally by Formulas (I) and (II) above. It should be noted that the products undergo transformation from the monomer of Formula (I) to the dimer of Formula (II) but that the formation of the dimer is favored when diols are selected for the organic compound reactant which have at least one hydroxyl group of the tertiary type, and that otherwise the formation of the monomer is favored.

The products obtained by the method of the present invention are molybdenum derivative compounds which are suitable for use as catalysts capable of catalyzing the oxygen transfer in a homogeneous phase from, for example, a peroxy compound of the type R—OOH, wherein R = hydrogen, alkyl, cycloalkyl, aryl, aralkyl or acyl, to an unsaturated compound of the type having the general formula:

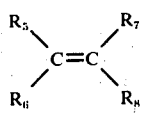

wherein each of $R_5$, $R_6$, $R_7$ and $R_8$, which may be the same or different, may be a hydrogen atom, an alkyl group having from one to eight carbon atoms, or an aryl, alkaryl, cycloalkyl, hydroxyalkyl or cyano-alkyl group, so as to give the corresponding epoxides.

The following examples illustrate embodiments of the present invention and illustrate the unexpectedly improved yield results as compared to the prior art methods of preparation:

EXAMPLE 1

This Example describes the preparation of a product which is predominantly the compound represented by Formula (I) above wherein $R_1 = R_2 = R_3 = = H$ and $R_4 = CH_3$, as prepared by a prior art method.

About 304.4 grams (4 moles) of propylene glycol is added to a three necked round bottom flask immersed in a heating bath maintained at a temperature of about 85° C. The flask is equipped with an air driven stirring paddle and a reflux condenser. About 144 grams (1 mole) of molybdenum trioxide is added to the flask and allowed to become wetted and dispersed by stirring. The reaction mixture is heated to about 90° C. to 95° C. and maintained at that temperature range for about 10 hours.

Next, undissolved molybdenum trioxide solids are removed from the product solution, while hot, via filtration. The undissolved molybdenum trioxide solids are washed with diethyl ether to recover adhering molybdenum derivative compound catalyst (ie., molybdenum diglycolate) and propylene glycol. The molybdenum diglycolate and propylene glycol which is washed from the undissolved trioxide solids is separated from the diethyl ether wash solution by evaporation and is returned to the product solution for purposes of making a complete material balance. As a practical matter, the production solution with the undissolved molybdenum trioxide solids filtered therefrom may generally be used as an efficient epoxidation catalyst.

Analysis shows that only about 20% of the molybdenum trioxide reactant is solubilized, i.e., a 20% yield based on molybdenum trioxide consumption is observed.

EXAMPLE 2

The method of Example 1 is repeated except that about 49 grams (about 0.5 moles) of concentrated sulfuric acid is added to the reaction mixture immediately after the molybdenum trioxide is added to the propylene glycol. The reaction appears to be unaffected by the sulfuric acid and a yield of 18% is observed.

EXAMPLE 3

The method of Example 2 is repeated except that about 20 ml. of concentrated HCl (8.8 grams or 0.24 moles of HCl) is added in place of the sulfuric acid to illustrate the present invention. The yield is determined to be 43%, more than twice that observed in Examples 1 and 2.

EXAMPLE 4

The method of Example 2 is repeated except that about 41.5 ml. of concentrated HCl (18.25 grams or about 0.5 moles of HCl) is used in place of the sulfuric acid to illustrate the present invention. A yield of 74% is observed.

The following table shows the unexpected and advantageous yield increases of the present invention over the prior art preparation methods:

| Example | Reactants | Catalyst | Yield (based on $MoO_3$ solubilized) |
|---|---|---|---|
| 1 | 4 moles propylene glycol and 1 mole molybdenum trioxide | None | 20% |
| 2 | Same | 0.5 moles $H_2SO_4$ | 18% |
| 3 (Present Invention) | Same | 0.24 moles HCl | 43% |
| 4 (Present Invention) | Same | 0.5 moles HCl | 74% |

What is claimed is:

1. In a method of preparing molybdenum derivative compound catalysts represented by one of the following formulas:

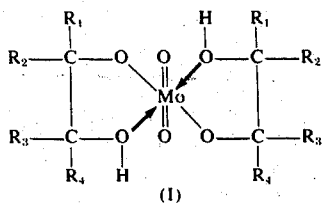

(I)

and

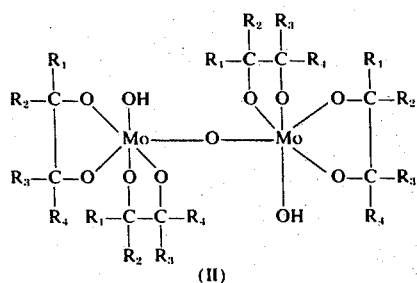

(II)

wherein each of $R_1$, $R_2$, $R_3$ and $R_4$, which may be the same or different, is a hydrogen atom, an unsubstituted or substituted hydrocarbon radical having from one to 10 carbon atoms, or a group having one of the formulas:

—COOR, —CN, —CONH$_2$, and —NO$_2$, where R is a hydrocarbon radical having from one to 10 carbon atoms, or where $R_1$ and $R_4$, and/or $R_2$ and $R_3$ may form a bivalent hydrocarbon radical, by reacting an oxygen-containing molybdenum compound selected from the group consisting of molybdenum acetylacetonate, molybdic acid and molybdenum oxides, with about 2 to about 20 moles of an organic compound having vicinal hydroxyl groups, per mole of molybdenum, the improvement which comprises carrying out the reaction in the presence of at least about 0.05 moles of hydrohalic acid, per mole of molybdenum, said hydrohalic acid being selected from the group consisting of hydrofluoric acid, hydrochloric acid, hydrobromic acid and hydroiodic acid.

2. The method of claim 1 wherein said organic compound is an alkylene glycol having about 2 to about 12 carbon atoms.

3. The method of claim 1 wherein said reaction is performed at a temperature from about −20° C. to about 110° C.

4. The method of claim 1 wherein said organic compound is an alkylene glycol having about 2 to about 6 carbon atoms.

5. The method of claim 1 wherein said hydrohalic acid is selected from hydrofluoric acid and hydrochloric acid.

6. The method of claim 1 wherein a compound having the structure of Formula (I) is prepared.

7. The method of claim 6 wherein said organic compound is an alkylene glycol having about 2 to about 12 carbon atoms.

8. The method of claim 7 wherein said reaction is performed at a temperature from about −20° C. to about 110° C.

9. The method of claim 6 wherein said organic compound is an alkylene glycol having about 2 to about 6 carbon atoms.

10. The method of claim 6 wherein said hydrohalic acid is selected from hydrofluoric acid and hydrochloric acid.

* * * * *